(12) United States Patent
Adel (10) Patent No.: US 9,381,399 B2
(45) Date of Patent: Jul. 5, 2016

(54) EXERCISE RECORDATION METHOD AND SYSTEM

(71) Applicant: Cellco Partnership, Arlington, VA (US)

(72) Inventor: Michael A. Adel, Parsippany, NJ (US)

(73) Assignee: Cellco Partnership, Basking Ridge, NJ (US)

(*) Notice: Subject to any disclaimer, the term of this patent is extended or adjusted under 35 U.S.C. 154(b) by 660 days.

(21) Appl. No.: 13/783,615

(22) Filed: Mar. 4, 2013

(65) Prior Publication Data

US 2014/0248996 A1  Sep. 4, 2014

(51) Int. Cl.
| | |
|---|---|
| *A63B 24/00* | (2006.01) |
| *G06Q 10/06* | (2012.01) |
| *A61B 5/00* | (2006.01) |
| *A61B 5/11* | (2006.01) |

(52) U.S. Cl.
CPC .......... *A63B 24/0062* (2013.01); *A61B 5/1126* (2013.01); *A61B 5/6895* (2013.01); *G06Q 10/0639* (2013.01); *A61B 2562/0219* (2013.01); *A61B 2562/0261* (2013.01)

(58) Field of Classification Search
CPC ................... A63B 24/0062; A63B 2024/0093; A63B 21/00; A63B 21/4029; A63B 22/00; A61B 2562/0219; A61B 2562/0261
See application file for complete search history.

(56) References Cited

U.S. PATENT DOCUMENTS

2008/0090703 A1* 4/2008 Rosenberg ............. A63B 24/00 482/8

* cited by examiner

*Primary Examiner* — Toan Le (57) ABSTRACT

An exercise reporting and maintenance system contains a device including a memory with a management application installed thereon. The application is configured to process a sensor signal including a total weight and movement speed, analyze the sensor signal by inputting the total weight and the movement speed into a monitoring heuristic to generate an output, and automatically transmit the output in real-time to be presented by a display system.

22 Claims, 6 Drawing Sheets

EXERCISE RECORDATION METHOD AND SYSTEM

In general, exercise and workout routines are manually recorded in notebooks. Manually recording notes is a tedious process that requires diligently recording aspects of each exercise immediately after completion. In addition, manually written notes are prone to getting lost or damaged. Therefore, it may be prudent to provide an automatic real-time exercise tracking system to replace manual recording.

DETAILED DESCRIPTION

An exemplary exercise tracking system and method may include a management application that detects in real-time exercise characteristics, such as weight and motion, via a sensor system to provide visual and/or auditory feedback via a computing system.

In an operational example, after the exemplary exercise tracking system and method is initiated, the computing system automatically accesses in real-time the sensor system to retrieve a sensor signal indicating a total weight of an exercise article or equipment. Next, while the exercise article or equipment is in use, the computing system automatically accesses in real-time the sensor system to retrieve a sensor signal indicating the motion of the exercise article or equipment. In turn, output devices of the computing system based on the sensor signal present real-time visual and/or auditory feedback.

A sensor system may include electronic circuitry that detects, converts, and transmits a sensor signal related to a weight and a motion of the exercise article or equipment. The sensor system may be adapted to integrate with or attach to the exercise article or equipment. The size, location, and shape of the sensor system and its components may vary according to the exercise article or equipment. The components of the sensor system may particularly include sensors that are connected wirelessly or via wires to a control circuit.

A sensor is a transducer that converts one form of energy, such as mechanical energy, to another, such as electrical energy. Sensor examples include but are not limited to tactile sensors, vibration powered generators, load cells, strain gauges, accelerometers, or the like and may be constructed from but not limited to conductive rubber, metallic capacitive sensing elements, and the like. Examples of energy that the sensor may convert or produce include mechanical energy, elastic energy, sound energy, thermal energy, chemical energy, electric energy, and the like.

For example, a tactile sensor may be a conductive rubber transducer that outputs an electrical signal in accordance with a pressure (e.g., an object contact force) applied perpendicularly to a contact area (e.g., a local portion of a contact surface) of the tactile sensor. That is, as the tactile sensor compresses and decompresses due to pressure increases and decreases, an electrical capacitance or resistance of the tactile sensor changes. The change in electrical capacitance or resistance is measured and outputted as an electrical signal.

For example, a strain gauge may be a metallic foil pattern device with an insulating flexible backing that outputs an electrical signal in accordance with a strain applied to an object (e.g., the exercise article or equipment). That is, as the strain gauge deforms in accordance with the object, the foil is deformed and causes an electrical resistance to change. The change in electrical resistance is measured and outputted as an electrical signal.

A wire may be a strand of metal that connects the components of sensor system in support of power and signaling (e.g., signals between a tactile sensor, an accelerometer, and a control circuit). A wire, along with the other components within the sensor system, may be protected by a para-aramid synthetic fiber (e.g., Kevlar®) wrap to prevent damage from the moving components of the exercise article or equipment.

A control circuit may be configured to generate a sensor signal based on the electrical signals received over the wires from the sensors. For example, the control circuit may generate a sensor signal that indicates the total weight and the motion of the exercise article or equipment. The control circuit may then transmit the sensor signal to the computing system via a transmission.

A transmission may be a wireless connection between two endpoints (e.g., a control circuit and a computing system) that carries signals. As wired and wireless transmissions both involve signaling, they thus may be substituted for each other in different applications of the exemplary exercise tracking system and method.

A computing system includes a central processing unit (CPU), a memory, a receiver, and may be any computing system and/or device, as further described below. The memory of computing system may store a management application configured to analyze the sensor signal. Further, the computing system may include output devices, such as a speaker and/or a display that present visual or auditory information based on a monitoring output generated by the management application. For example, once the sensor signal is retrieved or received by the computing system, the management application analyzes the sensor signal to calculate a monitoring output. The monitoring output, in turn, is utilized to generate and present real-time feedback via an output device.

A management application may store, manage, and execute monitoring heuristics. For example, utilizing monitoring heuristics, the management application analyzes a sensor signal to calculate monitoring outputs.

Monitoring heuristics are a suite of models and methodologies that utilize one or more sensor signals as an input to calculate one or more monitoring outputs. For example, because the sensor signal is based on the electrical signals of an accelerometer attached to an exercise article in motion, a monitoring heuristic may calculate an acceleration magnitude and direction for an exercise article or equipment from the sensor signal.

Monitoring heuristics may be configured to calculate any monitoring output, such as weight, motion, duration, repetition, and the like, in any measurement unit from the sensor signal. For example, a repetition number may be a monitoring output calculated by a monitoring heuristic based on detected changes in magnitude and direction for an exercise article or equipment. Further, as the repetition number increments according to the monitoring heuristic, the management application may also increment a counter on the display, thereby providing real-time visual feedback.

Figure 1A:
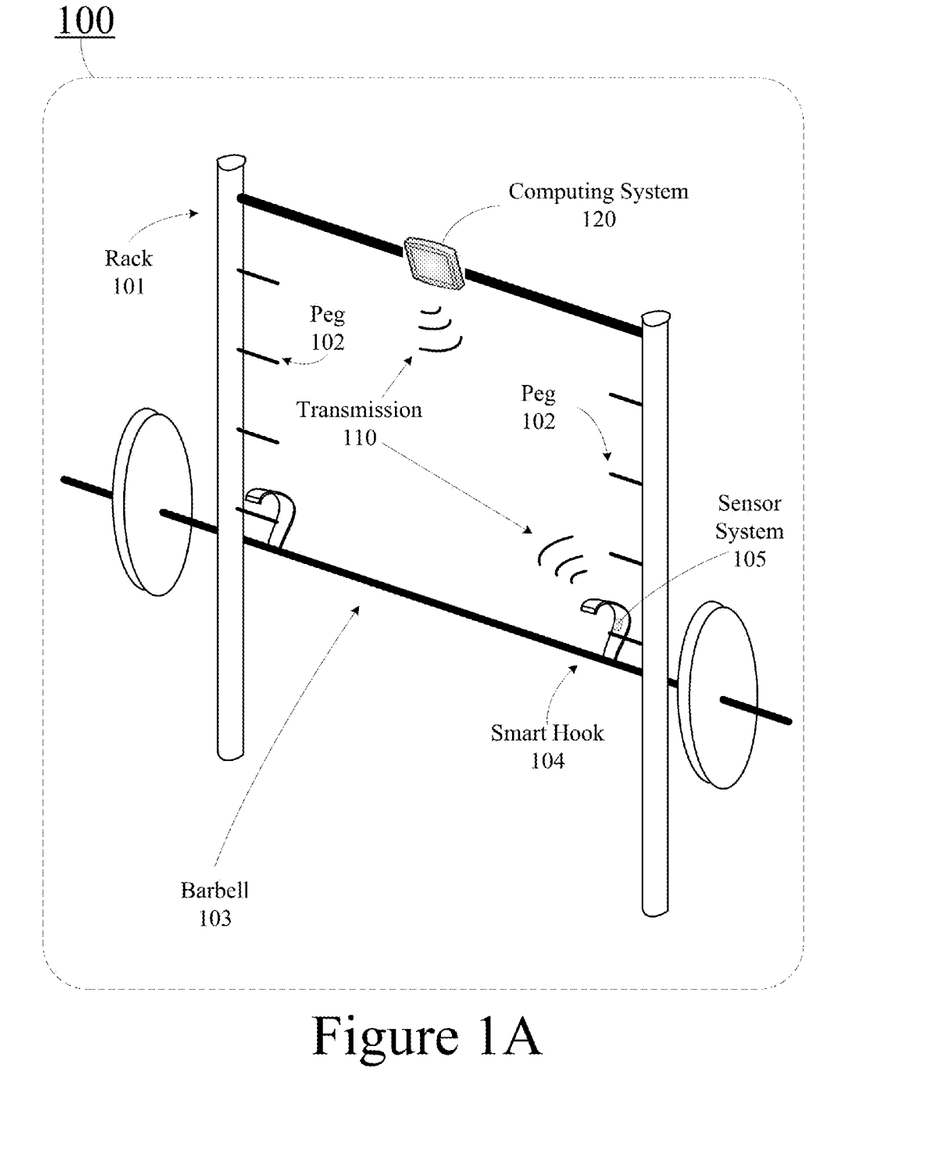
FIG. 1A-B illustrate an exemplary system in which exercise characteristics are detected.
Figure 1B:
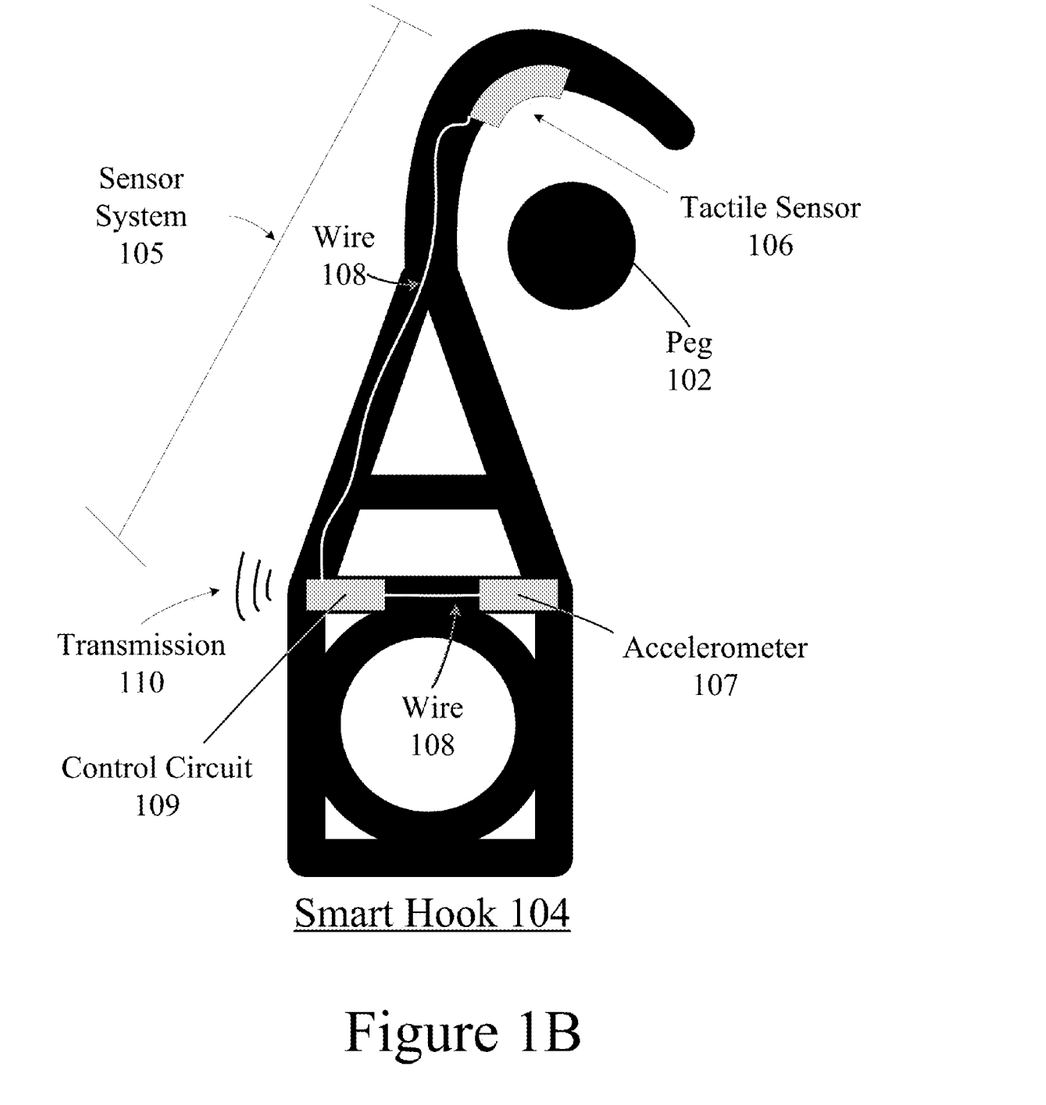

FIGS. 1A-B illustrate an exemplary exercise or workout tracking system 100 having a rack 101 that includes pairs of pegs 102 from which a barbell 103 hangs by a pair of hooks, including at least one smart hook 104. The smart hook 104 includes a sensor system 105 that communicates wirelessly (e.g., via transmission 110) with a computing system 120.

The exemplary systems shown in the figures may take many different forms and include multiple and/or alternate components and facilities, and while the exemplary systems are shown in the figures, the exemplary components illustrated in the figures are not intended to be limiting. Indeed, additional or alternative components and/or implementations may be used. For example, although the computing system 120 may be separate from the sensor system 105 while being connected via the transmission 110, the sensor system 105 and the computing system 120 may also be fully integrated and self-contained within a single device or housing. Also, the components of the exemplary tracking system 100 may be independently located in separate devices or housing, as further described below.

In operation, after the exemplary exercise tracking system 100 is initiated, the computing system 120 automatically retrieves a sensor signal from the sensor system 105 to calculate in real-time a total weight of the barbell 103, hooks, and attached weight (e.g., lifting plates). Further, while the user adds or subtracts weight to the barbell 103, the computing system 120 continues to retrieve the sensor signal from the sensor system 105 to calculate the total weight as it varies in real-time. Next, when the barbell 103 is lifted from the pair of pegs 102 and utilized for exercise (e.g., put into motion), the computing system 120 automatically retrieves the sensor signal from the sensor system 105 to calculate a motion of the barbell 103 in real-time.

Particularly, as illustrated in FIG. 1B, the sensor system 105 may include sensors, such as a tactile sensor 106 and an accelerometer 107, that are connected via wires 108 to a control circuit 109. While the barbell 103 is at rest and hanging from any pair of pegs 102, the tactile sensor 106 may generate an electrical signal based on the pressure between the smart hook 104 and a peg.

Additionally, the sensor system 105 may include a strain gauge as a sensor attached to the smart hook 104. For instance, the smart hook 104 may include a connection joint, a welding seam, etc. that the strain gauge may bridge. The strain gauge deforms as weight is added to the barbell. Therefore, while the barbell 103 is at rest, a change in electrical resistance may be measured as the foil of the strain gauge deforms in accordance with the smart hook 104 and outputted as an electrical signal.

Further, while the barbell 103 is in motion, the accelerometer 107 may generate an electrical signal based on the motion of the barbell 103. The control circuit 109 may receive the electrical signals from the tactile sensor 106 and the accelerometer 107 via wires 108 and utilize the electrical signals to generate a sensor signal.

As illustrated in FIG. 1A, a transmission 110 communicates the sensor signal between the control circuit 109 and the computing system 120, as it is being generated. That is, the computing system 120 may access and retrieve the sensor signal from the control circuit 109, or the control circuit 109 may then transmit the sensor signal to the computing system 120 via transmission 110. Note that although the figures illustrate transmission 110 as a wireless connection, transmission 110 may also be a wired connection.

The management application of computing system 120 next analyzes the sensor signal in real-time by utilizing the monitoring heuristics to calculate monitoring outputs.

An equipment profile may be a data structure for managing data and monitoring heuristics related to an exercise article or equipment. For instance, the equipment profile may be configured to govern the monitoring heuristics according to specifications contained within the equipment profile, such as a sensor configuration and dimensions of the exercise article or equipment. Equipment profiles may also be identified by a unique identifier (e.g., equipment serial or identification number).

For example, in the case of FIGS. 1A-B, the computing system 120 may also store a rack profile particular to the rack 101 and the barbell 103. The rack profile may include specifications, such as a sensor configuration of the smart hook 104, a spacing of the pair of pegs 102, and a length of the barbell. Therefore, the management application may utilize these specifications to generate a monitoring heuristic that may accurately calculate a total weight based on a detected pressure by a singular smart hook 104.

Further, the computing system 120 includes a display that may generate a user interface populated by the management application according to the monitoring outputs calculated in real-time, thereby presenting visual feedback during use of the exercise article (e.g., the barbell 103).

Thus, the exemplary tracking system 100 may provide a management application of a computing system 120 that retrieves a sensor signal from the sensor system 105. The management application may analyze the sensor signal according to monitoring heuristics associated with an equipment profile and generate a monitoring output that is processed by an output device.

In addition, the sensor system 105, computing system 120, or any combination thereof may include a power supply. A power supply may be any power source, such an internal power device consisting of one or more electrochemical cells that convert stored chemical energy into electrical energy and is configured to supply electricity to the components of the exemplary tracking system 100. The power supply may also be a power cord to an external power source in combination with or lieu of the internal power device. Further, when a power supply or an external source is not included in or connected to a first component of the exemplary tracking system 100, electricity may be supplied to the first component from a second component via a connection.

Figure 2:
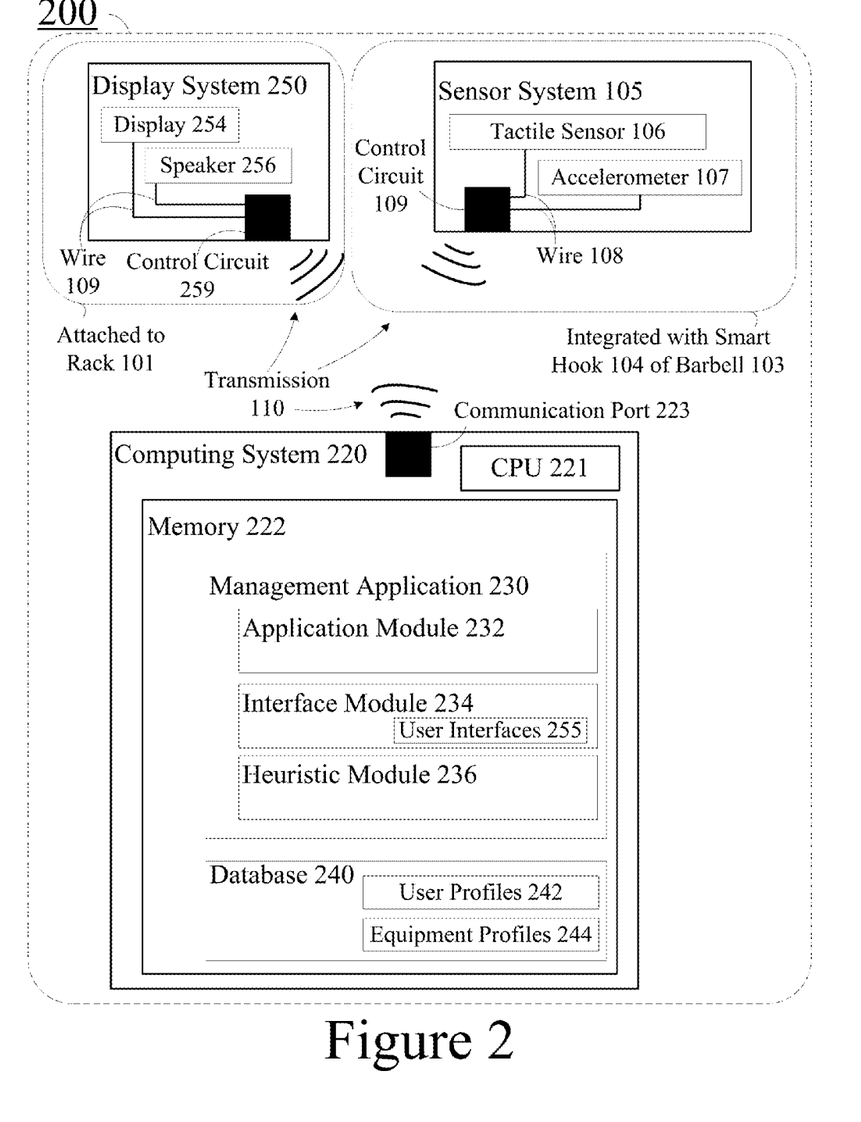
FIG. 2 illustrates an exemplary system that includes a management application installed on a memory of a computing system that generates a monitoring output based on sensor signals.

FIG. 2 illustrates an exemplary system 200 that includes a sensor system 105 that is integrated with a smart hook 104, a computing system 220, and a display system 250 that is attached to rack 101. Note that the same or equivalent elements as those of the FIG. 1A-b described above are denoted with similar reference numerals, and will not be described in detail with regard to FIG. 2.

In general, the exemplary system 200 is an example of the computing system 120 being separated into the computing system 220 and the display system 250. In this example, the computing system 220 interacts with the sensor system 105 and the display system 250, which act as terminals that receive transmissions 210 from a computing system 220. Further, in support of tracking exercise motions, the management application 230 of the exemplary system 200 may utilize user profiles 242 and equipment profiles 244 to, based on sensor signals from the sensor system 105, generate monitoring outputs for presentation by the display system 250.

For example, when a user with a computing system 220 (e.g., a hand held user device, such as a smartphone) approaches the rack 101, the computing system 220 initiates a connection (e.g., via Bluetooth® or Near Field Communication (NFC)) with the sensor system 105 and the display system 250. An equipment profile 244 identified by the computing system 220 based on the connection (e.g., the sensor system 105 provides an equipment serial number) is synced with a previously selected user profile 242 to complete a profile load. The computing system 220 then transmits a user interface 255 for display by the display system 250 that indicates system connectivity and a completed profile load (e.g., the exemplary system 200 is ready to provide exercise tracking services).

As the user prepares and utilize the exercise article (e.g., a barbell 103 resting on a rack 210), the management application 230 of the computing system 220 automatically accesses the sensor system 105 to retrieve a sensor signal and analyzes the sensor signal in real-time according to monitoring heuristics identified by the profile load. Further, the computing system 220 also automatically transmits a monitoring output in real-time to be presented by the display system 250, and tracks and records the exercise characteristics based on the monitoring heuristics in the previously selected user profile 242.

As indicated above, the exemplary systems shown in the figures may take many different forms and include multiple and/or alternate components and facilities. For example, the computing system 220 may be attached to a rack 101 (e.g., as illustrated in FIG. 1A) and include a touch screen display along with network connectivity. Thus, a user may operate the touch screen display to select and configure a user profile 242 and/or an equipment profile 244.

The attached computing system 220 may also include a near field communication component that may enable user recognition through the contact of another device that includes near field capabilities (e.g., an NFC card). Once contacted by the NFC card, the computing system 220 detects identification information of the NFC card and loads a corresponding user profile 242. Also, although the computing system 220 may be separate as illustrated in FIG. 2 from the sensor system 105 and the display system 250 while being networked for communication through connection 210, the sensor system 105, the computing system 220, and the display system 250 and may also be fully integrated and self-contained within a single device or housing.

A computing system 220 includes a central processing unit (CPU) 221, a memory 222, and a communication port 223. The memory 222 of computing system 220 stores a management application 230 comprising an application module 232, an interface module 234 (which generates user interfaces 255), and a heuristic module 236 along with a database 240 (which manages user profiles 242 and equipment profiles 244).

In one operational example, the computing system 220 receives at a communication port 223 a sensor signal generated and transmitted by the sensor system 105 via a transmission 110. In turn, the application module 232 of the management application 230 processes and forwards the sensor signal to the heuristic module 236. The heuristic module 236 may utilize user profiles 242 and equipment profiles 244 to select, generate, and apply monitoring heuristics to the sensor signal, which generate a monitoring output. The monitoring output is utilized by the interface module 235 to generate a user interface 255 and/or auditory signals, which the management application 230 transmits via the communication port 223 to the display system 250 for presentation by a display 254 or speaker 256.

Computing systems and/or devices, such as exemplary computing system 220 (and computing system 120), may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing devices include, without limitation, a smartphone, a mobile phone, a tablet device, a computer workstation, a server, a desktop, notebook, laptop, or handheld computer, or some other computing system and/or device.

Computing systems and/or devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc.

In general, a processor or a microprocessor (e.g., CPU 221) receives instructions from a memory (e.g., memory 222) and executes these instructions, thereby performing one or more processes, including one or more of the processes described herein. Such instructions and other data may be stored and transmitted using a variety of computer-readable media. The CPU 221 may also include processes comprised from any hardware, software, or combination of hardware or software that carries out instructions of a computer programs by performing logical and arithmetical calculations, such as adding or subtracting two or more numbers, comparing numbers, or jumping to a different part of the instructions. For example, the CPU 221 may be any one of, but not limited to single, dual, triple, or quad core processors (on one single chip), graphics processing units, visual processing units, and virtual processors. Similarly, control circuits 109, 209, 259 may also be a processor or microprocessor as described above.

The memory 222 may be, in general, may be any computer-readable medium (also referred to as a processor-readable medium) that may include any non-transitory (e.g., tangible) medium that participates in providing data (e.g., instructions) that may be read by a computing system (e.g., by a CPU 221 of a computing system 220). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computing system. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

The communication port 223 may include any connector used for digital or analog signal transfers. For instance, the communication port 223 may be any antenna technology that implements a wireless exchange of data, such as cellular, Bluetooth®, NFC, or the like, by converting propagating electromagnetic waves to and from conducted electrical signals. For example, the communication port 223 may be an antenna technology that implements Wi-Fi, which is the exchange data wirelessly using radio waves over a network, as described below.

The management application 230 may be software stored in the memory 222 of the computing system 220 that, when executed by the CPU 221 of the computing system 220, may manage user profiles 242 and equipment profiles 244 stored in the database 240, accumulate data from the sensor system 105 via the application module 232, generate data via the heuristic module 236, and generate user interfaces 255 via the interface module 234.

For example, the management application 230 may be configured to generate a user profile 242 by selecting, associating, and configuring monitoring heuristics congruent with the preferences and/or workout programs submitted via user interfaces 255 generated by the interface module 234. The management application 230 may also through its modules enable user profiles 242 to be stored in the database 240.

A user profile 242 may be a data structure for managing a user account, workout programs, and preferences. A user account may include user specific information, such as height, weight, range of motion, as well as additional log-on information for connection with other services (e.g., Facebook®, Twitter®, etc.). A workout program may include a set of pre-established or configured exercise routines that detail the repetitions, sets, and weight for an exercise. Preferences may be display and sound configurations that are employed by the display system 250 during an exercise. Further, each user profile 242 may include a unique identifier (e.g., user name or identification number) that may enable the management application 230 to access a database 240 and load a respective user profile 242. Each user profile 242 may also include equipment configurations, such that when a user profile 242 is loaded the equipment may automatically perform internal adjustments based on the unique aspects of the user (e.g., bench height). Thus, the user profile 242 may provide a mechanism that acts as a key to "unlock" exercise articles or equipment based on an authorization of a user profile 242. Each user profile 242 may also include data or mechanisms for managing personal goals and/or providing information to display personalized messages.

The management application 230 may also be configured to generate an equipment profile 244 by selecting, associating, and configuring monitoring heuristics congruent with the specifications contained within the equipment profile 244, as described above. The management application 230 may also through its modules enable equipment profile 244 to be stored in the database 240.

Further, as described above, the equipment profiles 244 may be configured to govern the monitoring heuristics according specifications contained within the equipment profile, as different exercise articles or equipment may embody different motions and ranges of motion.

For example, a leg-curl machine retro-fitted with a sensor system 105 may involve different exercise characteristics from the barbell 103, and thus require different calculations. That is, a range and a motion of a barbell exercise may be different than a range and a motion of a leg-curl machine retro-fitted with a sensor system 105 and display system 250. Therefore, when a user moves from the rack 101 with a barbell to the retro-fitted leg-curl machine, the equipment profile 244 may be change via the management application 230 to reflect the new exercise article or equipment (e.g., leg-curl machine) based on the connection established by the computing system 220.

Thus, the management application 230 may enable the setting of workout programs, units of measure, interactive counting systems, and the like for a user profile 242, along with configuring the monitoring heuristics for equipment profiles 244.

The management application 230 may through its modules also be configured to access the sensor system 105 to retrieve and analyze the sensor signal. Analysis of the sensor signal by the management application 230 includes applying the monitoring heuristics associated with the selected or preloaded user profile 242 and/or equipment profile 244 to the sensor signal. Thus, for example, the management application 230 may detect and track exercise motions based on a configuration of the workout programs, units of measure, interactive counting systems, and the like of a user profile 242.

The management application 230 may through its modules be configured to generate and transmit a monitoring output along with a user interface 255 to the display system 250 via the communication port 223.

For instance, the management application 230 may generate a monitoring output for a display 254 and/or a speaker 256. The management application 230 may also integrate the monitoring output with user interfaces 255 and display the integrated interfaces on a display local or external to the computing system 220.

For example, the management application 230 may through its modules be further configured to accumulate data, format the data and user interfaces 255 for displays other that the display 254, and transmit the data and user interfaces 255 via the communication port 223 to devices not included in exemplary system 200, as described in more detail below.

In addition, although FIG. 2 illustrates modular examples of the management application 230, where the modules 232, 234, and 236 may be software that when executed by the CPU 221 provides the operations described herein, the management application 230 and its modules 232, 234, and 236 may also be provided as hardware or firmware, or combinations of software, hardware and/or firmware. Additionally, although one example of the modularization of the management application 230 is illustrated and described, it should be understood that the operations thereof may be provided by fewer, greater, differently named, or differently located modules.

An application module 232 may include program code configured to facilitate communication between the modules of the management application 230 and hardware/software components external to the management application 230. For instance, the application module 232 may include program code configured to communicate directly with other applications, modules, models, devices, and other sources through both physical and virtual interfaces. That is, the application module 232 may include program code and specifications for routines, data structures, object classes, and variables that package and present data received from user interfaces 255 generated by the interface module 234 for transfer over a network or through a connection, as further described below. For example, the application module 232 may include program code for communication with a sensor system 105 and sending information to systems external to exemplary system 200.

An interface module 234 may include program code for generating and managing user interfaces 255 that control and manipulate the management application 230 based on a received input (e.g., user interfaces 255 is configured to select and configure monitoring heuristics, user profiles 242, and equipment profiles 244). For instance, the interface module 234 may include program code for generating, presenting, and providing one or more user interfaces 255 (e.g., in a menu, icon, tabular, map, or grid format) in connection with other modules for providing information (e.g., data, notifications, counters, instructions, etc.) and receiving inputs (e.g., user profile 242 and monitoring heuristic configurations). For example, the interface module 234 may display user interfaces 255 to provide information relative to the user profiles, such as graphical data detailing total weight lifted for the past daily, weekly, and/or monthly workout sessions, along with displaying tempo alerts and representations of the monitoring output.

Figure 3:
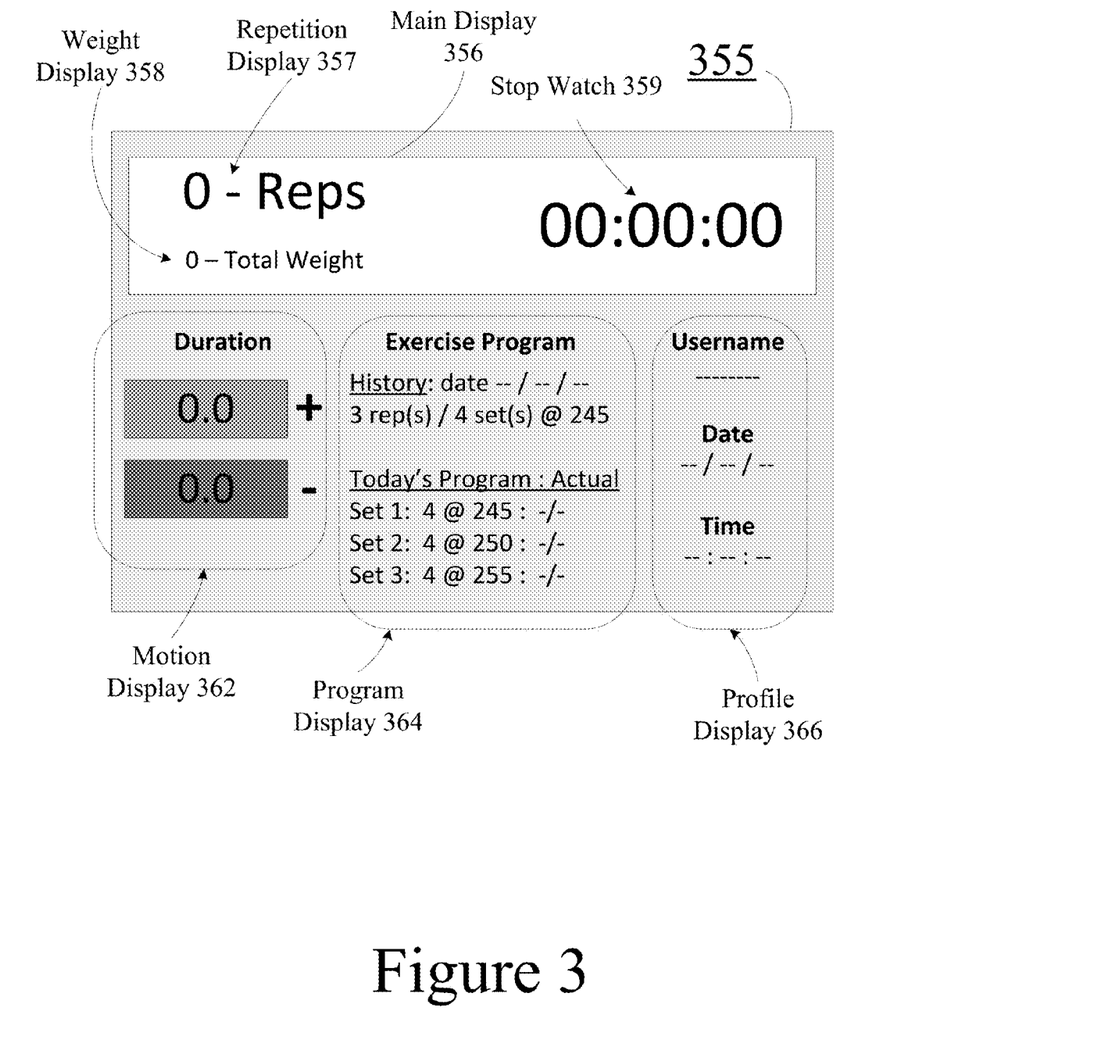
FIG. 3 illustrates an exemplary interface.

FIG. 3 illustrates an exemplary user interface 355 as generated by the interface module 234 of the management application 230. The exemplary user interface 355 is configured to present repetitions, a total weight, a stopwatch, a first or positive motion duration, a second or negative motion duration, historical data, current data, a username, a date, and a time in support of tracking exercise motions.

In general, the exemplary user interface 355 is includes a main display 356 that includes a repetition display 357, a weight display 358, and a stop watch 359. The exemplary user interface 355 also is includes a motion display 362, a program display 364, and a profile display 366.

In an operational example, the interface module 234 may utilize monitoring outputs to populate a main display 356 and motion display 362 of the exemplary user interface 355. The monitoring outputs generated by the management application 230 are based on sensor signals from the sensor system 105.

For example, one monitoring output indicates a number of repetitions (e.g., count a number of full exercise movements) and is presented by the repetition display 357. Another monitoring output indicates a total weight and is presented by the weight display 358.

Another monitoring output indicates a length of exercising time and is presented by a stop watch 359. The stop watch is triggered when the tactile sensor of the smart hook 104 fails to detect the presence of the pegs of the rack 101 (e.g., the barbell 103 is lifted) and stopped when the peg presence is detected (e.g., the barbell 103 is returned to the pegs).

Another monitoring output also indicates the duration and direction of a full exercise repetition and is presented by the motion display 362, where a first timer identified by a '+' may increment and flash green during a first motion and where a second timer identified by a '−' may increment and flash red during second motion. Regarding the duration and direction of each full exercise movement, the management application 230 may calculate the duration and direction of each exercise repetition based on the loaded profiles 242, 244 and the sensor signals.

The interface module 234 may further utilize a user profile 242 to populate the exemplary user interface 355. For example, historical data of the user profile 242 may be populated into the program display 364 (e.g., "History: date --/--/--" and "3 rep(s)/4 set(s) @ 245," where rep(s) is the number of exercise repetitions and set(s) is the number of grouped rep(s)), and current data of the user profile 242 may be populated into the profile display 366 (e.g., "Username --------," "Date --/--/--," and "Time --:--:--").

Moreover, user interfaces 255 (and 355) described herein may be provided as software that when executed by the CPU 221 provides the operations described herein, such as displaying tempo alerts and representations of the monitoring output. The user interfaces 255 may also be provided as hardware or firmware, or combinations of software, hardware, and/or firmware.

A heuristic module 236 may include program code configured to store, manage, and execute monitoring heuristics according to user and equipment profiles 242, 244. The heuristic module 236 may include program code configured to utilize the monitoring heuristics to analyze a sensor signal to determine exercise characteristics related to a weight and a motion in real-time.

Exercise characteristics may generally include weight or resistance, direction, speed, and duration. The sensor system 105 may generally include sensors that detect and convert theses exercise characteristics into electrical energy (e.g., the sensor signal). The sensor signal is the variable input utilized by the heuristic module 236 for monitoring heuristics, which in turn generate a monitoring output. The monitoring output is exercise feedback data that may be presented through a display system 250 or recorded in the database 220.

For example, the heuristic module 236 may calculate a force applied to a barbell 103 during a bench press by utilizing a pressure detected by the tactile sensor 106 and acceleration magnitude and direction detected by the accelerometer 107 of the barbell 103 from a rest position slightly above a chest to a peak position at arm's length from the chest.

Further, the heuristic module 236 may also calculate a force applied to a leg-curl machine, which includes an ankle pad, retro-fitted with a sensor system 105. The weight of the leg curl machine is generally adjusted by moving a pin to an appropriate weight plate attached to a cable system and may be detected based on a pin sensor preprogrammed to transmit a sensor signal based on the pin selected weight plate. The acceleration magnitude and direction may be detected by an accelerometer attached to the cable system. Thus, when the leg-curl machine is prepared and the ankle pad is moved, which may enable the cable system to manipulate the weight set by the pin, the monitoring heuristics utilize the pin location and cable system motion to calculate the force applied to the ankle pad.

A database 240 may include any type of data or file system (e.g., user profiles 242 and/or equipment profiles 244) that operates to support the management application 230.

In general, databases, data repositories or other data stores, such as database 240, described herein may include various kinds of mechanisms for storing, providing, accessing, and retrieving various kinds of data, including a hierarchical database, a set of files in a file system, an application database in a proprietary format, a relational database management system (RDBMS), etc. Each such data store may generally be included within a computing system (e.g., computing system 220) employing a computer operating system such as one of those mentioned above, and are accessed via a network or connection in any one or more of a variety of manners. A file system (e.g., user profiles 242 and equipment profile 244) may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In addition, as indicated in FIG. 2, database 240 includes user profiles 242 and equipment profile 244 and may be provided as software stored on the memory 222 of computing system 220. Database 240 may also be provided as hardware or firmware, or combinations of software, hardware and/or firmware. For example, as indicated in FIG. 4, databases 240a-b may be a computing device, as described above, including a CPU and memory that is separate from a computing system 420.

The display system 250 comprises a display 254, wires 109, and a control circuit 259, where the control circuit 259 communicates with the computing system 220 via the transmission 110. The display system 250 may also include a display 254 and a speaker 256. In one operational example, the speaker 256 may produce a sound indicating a tempo of an exercise to assist in maintaining an exercise pace while providing real-time feedback regarding pace via the display 254 (e.g., presenting the duration and direction of a full exercise repetition by the motion display 362).

Further, in some examples, the computing system 220 elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

Figure 4:
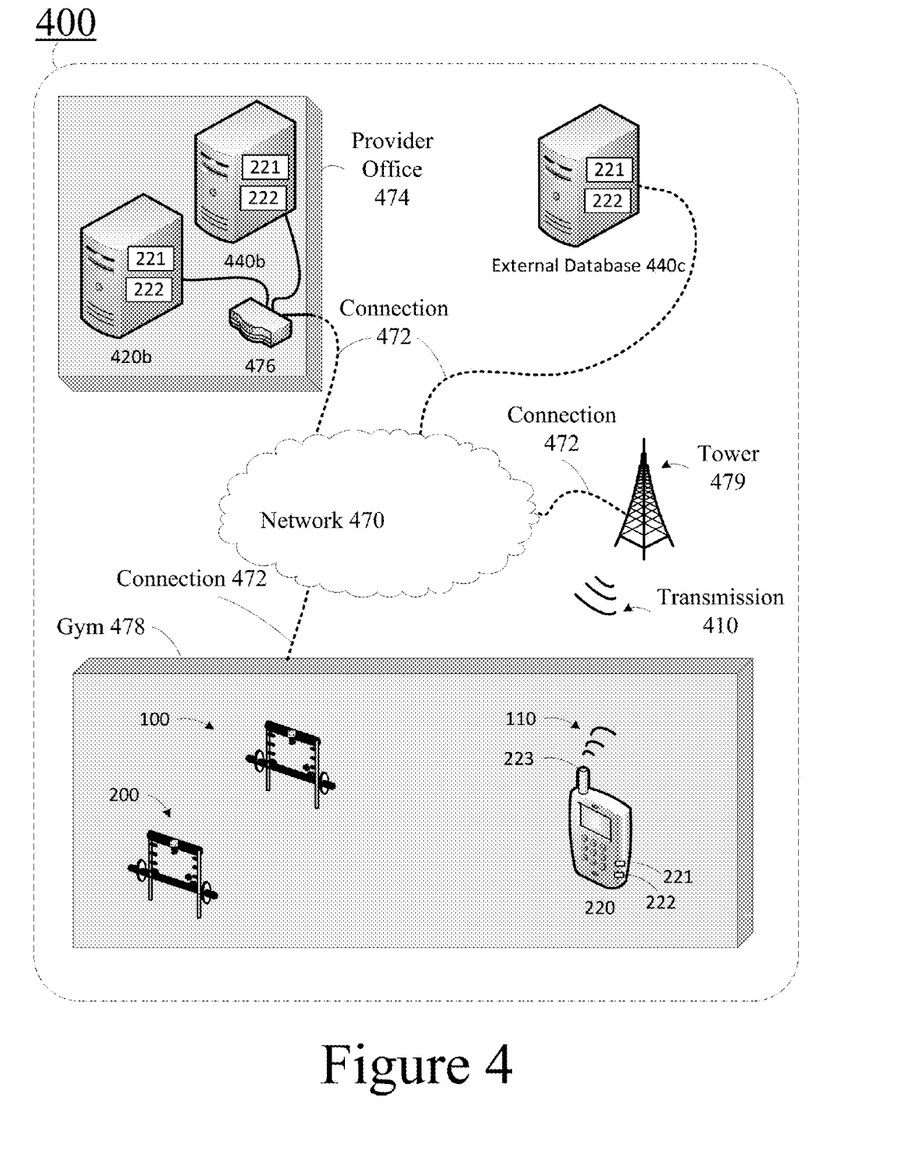
FIG. 4 illustrates an exemplary system.

FIG. 4 illustrates a chronicle service 400 having multiple exemplary tracking systems 100, 200, computing systems, and databases. FIG. 4 further illustrates an exemplary chronicle service 400 including the provider office 434 that manages and supplies data, profiles, and monitoring heuristics to a computing system 220 and exemplary tracking systems 100, 200.

For instance, the exemplary chronicle service 400 illustrates a network 470 that provides connections 472 to a provider office 474 and a gym 478, which includes two exemplary systems 100 and 200. Further, a computing system 220 communicates with a tower 479 to access the systems and resources connected to the network 470. Note that the same or equivalent elements as those of the Figures described above are denoted with similar reference numerals, and will not be described in detail with regard to FIG. 4.

In one operation example, the user may approach any systems 100, 200, at the gym 478 with the computing system 220 in hand. If the user approaches system 100, the user may utilized the touch screen to select and configure their respective user profile 242 and/or an equipment profile 244 locally stored within the system 100. Further, the provider office 474 and the gym 478 may be in communication with the system 100 to provide user profile 242 and/or an equipment profile 244 remotely stored within the chronicle service 400 for selection. A user may also indirectly configure the system 100 from the computing system 220 by utilizing the tower 479 and network 470.

Similarly, user profiles may be loaded in the same manner if the user approaches system 200. Further, the computing system 220 may also directly sync with the approached system 200 while accessing profile information stored locally or remotely, such as on the database 440b of the provider office 474. In effect, regardless of which tracking system is approached and/or a geographic location, the exemplary chronicle service 400 may be a connected exercise service that detects exercises performed with one of the systems 100, 200 through network connections or the computing system 220 and provides data recording.

Thus, the provider office 434 may supply profiles 242, 244 to and track exercises at the exemplary tracking systems 100, 200 by utilizing a wide area network (e.g., network 470) that includes multiple exercise facilities (e.g., gym 478) with local area networks to connect to respective sensor systems 105 and computing systems 220. In turn, a user may utilize any device such as their smartphone, a gym 478 provided computing system or NFC card, or the local system interface to select, trigger, and/or load a user profile 242 unique to the user.

For example, a user may utilize a local interface on a first system 100 at an exercise facility in Detroit, Mich. to load a personal user profile 242 and record a first workout, where the personal user profile 242 is updated according at the provider office 474. On a second day, a user may utilize a gym NFC card to initialize a second system 200 at an exercise facility in Washington, D.C., where the personal user profile 242 is also updated at the provider office 474 with the second workout. On a third day, the user may utilize their smartphone (e.g., a computing system 220) to initialize a third system 200 at a gym 478 in Philadelphia, Pa. During the initialization of the third system 200, the user profile 242 that has been previously updated from other locations is utilized to configure the third system 200. Therefore, any particular setting configuration made by the user in Detroit or Washington may automatically be implemented in Philadelphia.

A network 470 may be a collection of computers and other hardware to provide infrastructure to carry communications. For instance, the network 470 may be an infrastructure that generally includes edge, distribution, and core devices and provides a path for the exchange of information between different devices and systems (e.g., between the computer system 420a-b). Further, the network may be any conventional networking technology. For instance, network 470 may, in general, be any packet network (e.g., any of a cellular network, global area network, wireless local area networks, wide area networks, local area networks, or combinations thereof, but may not be limited thereto) that provides the protocol infrastructure to carry communications between multiple computing systems, databases, and at-home systems.

Connections 472 may be wired or wireless connections between two endpoints (devices or systems) that carry electrical signals that facilitate virtual connections. Virtual connections are the protocol infrastructure that may enable communication to and from the multiple computing systems, databases, and systems of FIG. 4.

A provider office 474 may be the location of an exercise tracking service provider. The provider office 474 may perform the role of a monitor facility that gathers and process data in support of exercise tracking services.

The provider office 474 may also generally include a computing system 420b which performs server operations for computing systems that do not have a full management application installed thereon (e.g., computing system 220). That is, the computing systems 420b may provide operational use of its resources to computing systems outside of the provider office 474. The provider office 474 includes a database 440b, which is separate from computing system 420b and which communicates with the computing system 420b to supply the full operational capabilities of a management application. Further, the provider office 474 may automatically compile user profiles to enhance the monitoring heuristic employed by the management application across the chronicle service 400.

The provider office 474 may also manage and transfer profiles 242, 244 along with management application 230 updates. For example, the provider office 474 may transfer an equipment profile 244, management application updates 120, and the like to the systems 100, 200 and the computing system 220 and enable the downloading of the same. Thus, the provider office 474 may be configured to provide two-way communications of information based on a collective assembly of knowledge for an exercise article or equipment.

In addition, the provider office may utilize a redundant system in external database 440c. Further, external database 440c is available to computing systems that either cannot access the necessary resources at the provider office 474 or that are particularly assigned to the database 420b. For instance, computing system 220 may be assigned to access data and information directly from external database 440c in support of tracking exercise services. Note that external database 440c, although related to computing system 420b and database 440b, is not physically located within the provider office 474 or gym 478.

A network device 476 may be an edge, a distribution, or a core device that is a gateway of a path between the network 470 and provider office 474.

A tower 479 may be a tall structure designed to support antennas or aerials for telecommunications along with communication ports for additional computing systems. Thus, the tower 479 may enable wired or wireless connections 472 that carry signals to or from the network 470 (e.g., a connection from the network 470 via the tower 479 to the computing system 420b). For example, the tower 479 may enable a computing system 420b to connect to and access the systems, devices, and data associated within the network 470 providing the computing system 420b is located within the range of tower 479.

Figure 5:
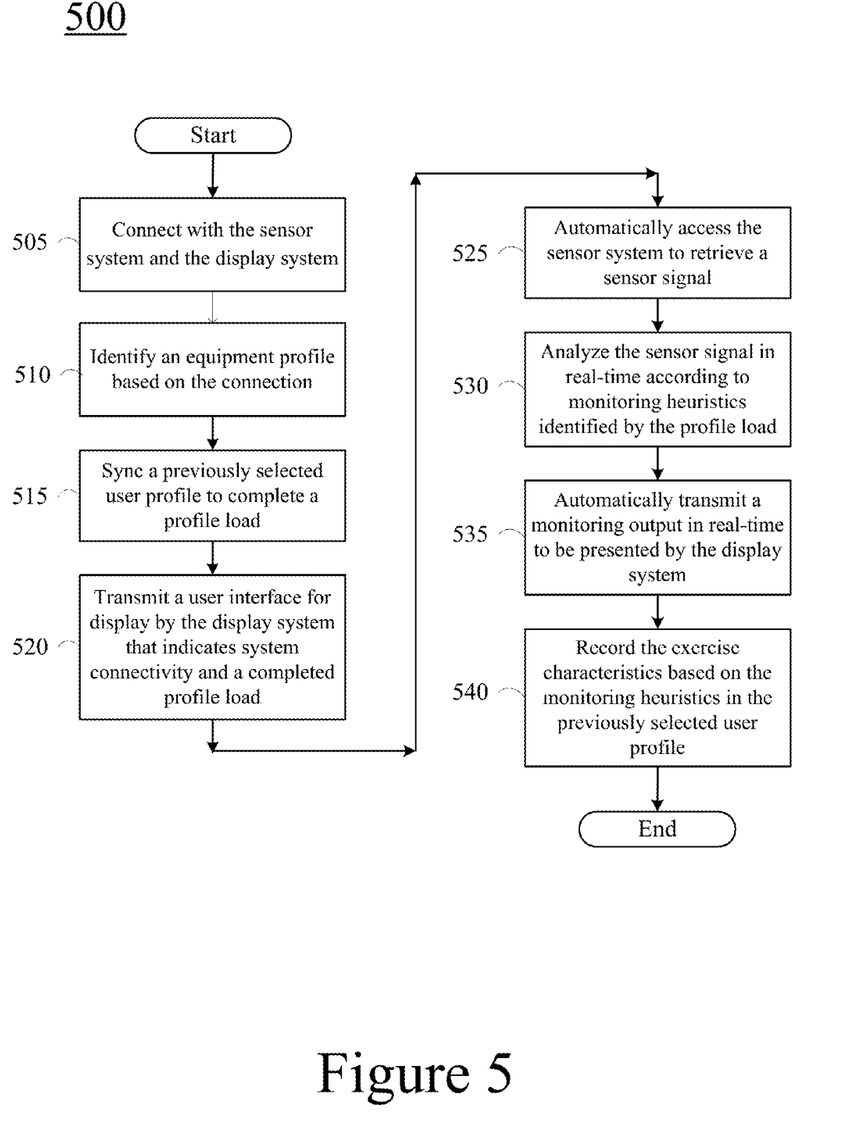
FIG. 5 illustrates an exemplary process flow executed by a management application.

FIG. 5 illustrates an exemplary process flow 500 executed by the management application 230 to connect 505 with the sensor system 105 and the display system 250; identify 510 an equipment profile 244 based on the connection; sync 515 a previously selected user profile 242 to complete a profile load; transmit 520 a user interface 255 for display by the display system 250 that indicates system connectivity and a completed profile load; automatically access 525 the sensor system 105 to retrieve a sensor signal; analyze 530 the sensor signal in real-time according to monitoring heuristics identified by the profile load; automatically transmit 535 a monitoring output in real-time to be presented by the display system 250; and record 540 the exercise characteristics based on the monitoring heuristics in the previously selected user profile 242.

The process flow begins by proceeding to block 505 where, for example, the management application 230 connects 505 with the sensor system 105 and the display system 250. For example, the computing system 220 (e.g. a smartphone with NFC capabilities) is brought within range of a NFC component of a display system 250 attached to a rack 101. Once within range, the computing system 220 detects the NFC component of the display system 250 and connects with the display system 250 attached to the rack 101 and the sensor system 105 integrated into the smart hook 104. Next, the exemplary process flow 500 proceeds to block 515.

In block 510, the management application 230 identifies an equipment profile 244 based on the connection. For example, the management application 230 utilizes the connection to access a control circuit 109 of the sensor system 105 and extract an equipment serial number. Utilizing the equipment serial number, the management application 230 accesses a database 220 and loads a corresponding equipment profile. Next, the exemplary process flow 500 proceeds to block 515.

In block 515, the management application 230 syncs a previously selected user profile 242 with corresponding equipment profile 244 to complete a profile load. For example, when a user has downloaded the management application 230 onto their smartphone (e.g., computing system 220), the set up a default user profile that was stored in database 240. The default user profile is synced with the corresponding equipment profile to complete a full profile load (e.g., to complete an imitation procedure for exercise tracking). In addition, the user may select a different profile, such as a lifting buddy's profile, from the default profile so that the lifting buddy may track their exercise motion using the same smartphone. Next, the exemplary process flow 500 proceeds to block 520.

In block 520, the management application 230 transmits a user interface 255 for display by the display system 250 that indicates system connectivity and a completed profile load. For example, the interface module 234 of the management application 230 may generate an initiation user interface that displays "INITIATION COMPLETE—READY TO TRACK YOUR MOTIONS" for a predetermined amount of time (e.g., five seconds). The initiation interface may then be transmitted to the display system 250 and present by the display 254. If the profile load did not correctly complete, the management application 230 transmits an error interface indicating that there is a problem and the system is not working.

After the predetermined amount of time, the interface module 234 may generate the exemplary user interface 355 for presentation by the display 254. Additionally, the interface module 234 may generate personalized messages and interfaces based on the profile used in the profile load for presentation by the display 254 any time after the profile load. For instance, the personalized messages may include messages that indicate a workout for a desired strength training, endurance program, etc. that may motivate a user to improve upon their previous workout. For example, after the initiation user interface is displayed, a motivation user interface may display "Last Time 10 reps of 80 lbs, TRY 12 REPS TODAY." In another example, a motivation user interface may display a comparison message, chart, and/or graph presenting the workout programs of other users alongside the current user's workout program, so that the current user may have a real-time indication as to their fitness level, rank, and/or status among those using the chronicle service 400. Next, the exemplary process flow 500 proceeds to block 525.

In block 525, the management application 230 automatically accesses the sensor system 105 to retrieve a sensor signal. For example, the management application 230 retrieves a total weight detected by the tactile sensor 106 and a movement speed detected by the accelerometer 107 via the control circuit 109. Based on this, the management application 230 may provide feedback to improve the workout, such as indicating that too much weight is being used (e.g., sensed by low speed or excessive tilting in a bench press). Next, the exemplary process flow 500 proceeds to block 530.

In block 530, the management application 230 analyzes the sensor signal in real-time according to monitoring heuristics identified by the profile load. For example, the management application 230 utilizes monitoring heuristics to calculate a force applied during an exercise based on the total weight detected by the tactile sensor and the acceleration detected by the accelerometer. Next, the exemplary process flow 500 proceeds to block 535.

In block 535, the management application 230 automatically transmits a monitoring output in real-time to be presented by the display system 250. For example, the interface module 234 of the management application 230 may continue to populate the exemplary user interface 355 presented on the display 254 based on the analyzed sensor signal. This continued population of the exemplary user interface 355 may be one aspect of an interactive counting system employed by the management application 230. Additionally, the interactive counting system of the management application 230 may use auditory means to guide an exercise tempo. Next, the exemplary process flow 500 proceeds to block 540.

In block 540, the management application 230 records the exercise characteristics based on the monitoring heuristics in the previously selected user profile 242. For example, the management application parses the exercise characteristics of speed, duration, weight, repetitions, range of motion (e.g., new exercise information), and sets from the monitoring output of the monitoring heuristics and loads them into a user profile 242.

Further, management application may automatically load the new exercise information of the user profile 242 with an online service, such as any social networking platform. Thus, the management application may automatically update tracking systems, leaderboards, or Facebook® profiles with the exercise information. Automatically updating tracking systems may thus provide a networked-enabled exercise system where institutions and businesses, such as universities, sport teams tracking, etc., may track the athletic progress of their employees/students/friends.

Next, the exemplary process flow 500 ends.

Thus, using this exemplary exercise tracking system and method, a user may instantly get feedback through video displays or speakers, while easily tracking exercise progress via their Smartphone or online social networks.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system, comprising:
a smart hook with a housing configured to couple with a peg of the equipment; and
a device including a hardware processor and a memory with a management application installed thereon, wherein the device is configured to:
automatically retrieve, from the smart hook, a sensor signal including a total weight and a movement speed of a piece of exercise equipment; and
generate in real-time a monitoring output based on a monitoring heuristic processing the sensor signal; and
automatically transmit in real-time the monitoring output to be presented by a display system.

2. The system of claim 1, wherein the management application retrieves the sensor signal from a sensor system, the sensor system comprising:
a tactile sensor configured to detect the total weight of the piece of the exercise equipment based on a pressure between the smart hook and the peg of the equipment.

3. The system of claim 1, wherein the management application retrieves the sensor signal from a sensor system, the sensor system comprising:
a pin sensor configured to detect the total weight of the piece of the exercise equipment based on a location of a pin of the equipment.

4. The system of claim 1, wherein the management application retrieves the sensor signal from a sensor system, the sensor system comprising:
an accelerometer configured to detect the movement speed of the piece of the exercise equipment.

5. The system of claim 1, the smart hook further comprising:
a sensor configured to detect the total weight of the piece of the exercise equipment and generate a first electrical signal in accordance with the total weight,
an accelerometer configured to detect the movement speed of the piece of the exercise equipment and generate a second electrical signal in accordance with the movement speed, and
a control circuit configured to generate the sensor signal based on the first and second electrical signals.

6. The system of claim 5, wherein the sensor is a tactile sensor configured to detect the total weight of the piece of the exercise equipment based on a pressure between an under portion of the smart hook and an upper portion of the peg of the equipment.

7. The system of claim 5, wherein the sensor is a strain gauge configured to detect the total weight of the piece of the exercise equipment based on a deformation of the smart hook.

8. The system of claim 1, wherein the display system comprises:
a display configured to, based on the monitoring output, present a user interface configured to provide in real-time a duration and a direction of an exercise repetition.

9. The system of claim 1, wherein the display system comprises:
a speaker configured to, based on the monitoring output, produce a tone in accordance with a tempo designated by a user exercise or an equipment profile.

10. A method, comprising:
automatically retrieving, by an electronic device and from a smart hook with a housing configured to couple with a peg of a piece of exercise equipment, a sensor signal including a total weight and a movement speed of the piece of exercise equipment;
generating in real-time a monitoring output based on a monitoring heuristic processing the sensor signal; and
automatically transmitting in real-time the monitoring output to be presented by a display system.

11. The method of claim 10, wherein automatically retrieving the sensor signal includes:
detecting the total weight of the piece of the exercise equipment based on the pressure between the smart hook and the peg of the equipment.

12. The method of claim 10, wherein automatically retrieving the sensor signal includes:
detecting the total weight of the piece of the exercise equipment based on a location of a pin.

13. The method of claim 10, wherein automatically retrieving the sensor signal includes:
detecting the movement speed of the piece of the exercise equipment based on an electrical output of an accelerometer.

14. The method of claim 10, further comprising:
  detecting, by a sensor of the smart hook, the total weight of the piece of the exercise equipment and generating a first electrical signal in accordance with the total weight,
  detecting, by an accelerometer of the smart hook, the movement speed of the piece of the exercise equipment and generating a second electrical signal in accordance with the movement speed, and
  generate, by a control circuit of the smart hook, the sensor signal based on the first and second electrical signals.

15. The method of claim 14, wherein the sensor is a tactile sensor that detects the total weight of the piece of the exercise equipment by detecting a pressure between an under portion of the smart hook and an upper portion of the peg of the equipment.

16. The method of claim 14, wherein the sensor is a strain gauge that detects the total weight of the piece of the exercise equipment by detecting a deformation of the smart hook.

17. The method of claim 10, further comprising:
  displaying, by the display system, a user interface configured to provide in real-time a duration and a direction of an exercise repetition.

18. The method of claim 10, further comprising:
  producing, by the display system, a tone in accordance with a tempo designated by a user exercise or an equipment profile.

19. A system, comprising:
  a sensor system with a housing integrated with a piece of exercise equipment and configured to:
    detect a total weight of the piece of the exercise equipment and generate a first electrical signal in accordance with the total weight;
    detect a movement speed of the piece of the exercise equipment and generate a second electrical signal in accordance with the movement speed;
    generate and transmit a sensor signal based on the first and second electrical signals to a computing system configured to analyze the sensor signal to produce in real-time a monitoring output; and
  wherein the sensor system includes at least one of:
    a tactile sensor configured to detect the total weight of the piece of the exercise equipment based on a pressure between an under portion of a smart hook and an upper portion of a peg of the equipment; and
    a strain gauge configured to detect the total weight of the piece of the exercise equipment based on a deformation of a smart hook.

20. The system of claim 19, wherein the sensor system further includes the tactile sensor configured to detect the total weight of the piece of the exercise equipment based on the pressure between the under portion of the smart hook and the upper portion of the peg of the equipment.

21. The system of claim 19, wherein the sensor system further includes the strain gauge configured to detect the total weight of the piece of the exercise equipment based on the deformation of the smart hook.

22. The system of claim 19, further comprising:
  the computing system including a memory with a management application installed thereon, wherein the computing system is configured to:
    connect with the sensor system to identify an equipment profile;
    sync a default profile with the equipment profile to complete a profile load; and
    record exercise characteristics based on the monitoring output in the default profile.

* * * * *